US012605304B2

(12) United States Patent
Ricci

(10) Patent No.: US 12,605,304 B2
(45) Date of Patent: Apr. 21, 2026

(54) DOSING SYRINGE

(71) Applicant: PLATINUM PHARMA SERVICE S.R.L.S., Citta' Sant'Angelo (IT)

(72) Inventor: Alfredo Ricci, Citta' Sant'Angelo (IT)

(73) Assignee: PLATINUM PHARMA SERVICE S.R.L.S., Citta' Sant'Angelo (IT)

( * ) Notice: Subject to any disclaimer, the term of this patent is extended or adjusted under 35 U.S.C. 154(b) by 1008 days.

(21) Appl. No.: 17/778,176

(22) PCT Filed: Jan. 7, 2021

(86) PCT No.: PCT/IB2021/050083
§ 371 (c)(1),
(2) Date: May 19, 2022

(87) PCT Pub. No.: WO2021/144668
PCT Pub. Date: Jul. 22, 2021

(65) Prior Publication Data
US 2022/0347056 A1 Nov. 3, 2022

(30) Foreign Application Priority Data

Jan. 14, 2020 (IT) ........................ 102020000000556

(51) Int. Cl.
*A61J 7/00* (2006.01)
*A61M 5/31* (2006.01)
*A61M 5/315* (2006.01)

(52) U.S. Cl.
CPC .... *A61J 7/0053* (2013.01); *A61M 2005/3126* (2013.01); *A61M 5/31525* (2013.01); *A61M 5/31533* (2013.01)

(58) Field of Classification Search
CPC ........ A61J 7/0053; A61M 5/178; A61M 5/31; A61M 5/31525; A61M 5/3153;
(Continued)

(56) References Cited

U.S. PATENT DOCUMENTS 5,344,409 A 9/1994 Ennis, III et al.
9,775,950 B2 * 10/2017 Creaturo ............. A61M 5/3243
(Continued)

FOREIGN PATENT DOCUMENTS

WO 2008016381 A1 2/2008
WO 2009095735 A1 8/2009
WO 2014162551 A1 10/2014

OTHER PUBLICATIONS

International Search Report mailed on Mar. 16, 2021, in corresponding to International Application No. PCT/IB2021/050083; 4 pages.
(Continued)

*Primary Examiner* — Chelsea E Stinson
*Assistant Examiner* — Alexandra Lalonde
(74) *Attorney, Agent, or Firm* — Maier & Maier, PLLC

(57) ABSTRACT

A dosing syringe including a hollow cylindrical body and a plunger slidable within the hollow cylindrical body. The dosing syringe includes at least one slider slidable within a distal flange of the hollow cylindrical body transversely to the hollow cylindrical body and at least one wall is formed in the plunger for abutting and blocking the at least one slider during sliding of the at least one slider within the distal flange, wherein the at least one wall provides a mechanical stop which stops a stroke of the plunger at a predetermined volume of product to be aspirated and/or dispensed.

13 Claims, 11 Drawing Sheets

(58) Field of Classification Search

CPC .......... A61M 5/31533; A61M 5/31535; A61M 5/31536; A61M 5/31541; A61M 5/31548; A61M 5/31545; A61M 5/31591; A61M 5/3156; A61M 5/31526; A61M 5/31595; A61M 2005/3125; A61M 2005/3126; A61M 2005/3142; A61M 2005/3154

See application file for complete search history.

(56) References Cited

U.S. PATENT DOCUMENTS

| | | | |
|---|---|---|---|
| 2006/0184136 A1* | 8/2006 | Kleyman | .......... A61M 5/31595 604/210 |
| 2011/0118701 A1* | 5/2011 | Baney | ............... A61M 5/31526 604/506 |
| 2018/0214638 A1* | 8/2018 | Hassanzadeh | ........ B01L 3/0241 |

OTHER PUBLICATIONS

Written Opinion of the International Searching Authority mailed on Mar. 16, 2021, in corresponding to International Application No. PCT/IB2021/050083; 6 pages.

\* cited by examiner

100; 1100; 2100; 3100

20; 120; 220; 320

30; 130; 230; 330

51

50

10; 110; 210; 310

14; 114; 214; 314

52

100; 1100; 2100; 3100

151

20; 120; 220; 320

30; 130; 230; 330

150

10; 110; 210; 310

14; 114; 214; 314

152

52

DOSING SYRINGE

CROSS-REFERENCE TO RELATED APPLICATIONS

This application is a National Stage of PCT/IB2021/050083, filed Jan. 7, 2021, which claims foreign priority to Italian Patent Application IT102020000000556, filed Jan. 14, 2020, the disclosures of each of which are incorporated herein by reference.

TECHNICAL FIELD

The present invention generally relates to the technical field of dosing syringes. More in particular, the present invention relates to a dosing syringe for aspirating and/or dispensing controlled and repeated doses of a product in liquid or semi-liquid form, typically a pharmaceutical product.

BACKGROUND

Dosing syringes are widely used to administer doses of pharmaceutical products, in particular to children and/or subjects with poor hand mobility. They represent a growing market, both due to the increase in subjects with mobility problems in their upper limbs and because the issue of the correct dosing of pharmaceutical products is increasingly perceived both by pharmaceutical companies and the subjects who use the pharmaceutical products.

A dosing syringe typically comprises a hollow cylindrical body, preferably transparent, and a plunger that is slidable within the hollow cylindrical body to enable aspiration into the hollow cylindrical body, and subsequently dispensing from the hollow cylindrical body, of a predetermined dose of pharmaceutical product. The plunger is provided with a head adapted to enable a user of the syringe to impart the necessary force to make the plunger slide within the hollow cylindrical body. On the outer surface of the cylindrical body there is also a graduated scale, which enables the user to aspirate only the necessary dose of pharmaceutical product.

A problem that usually arises when using a dosing syringe of the known type is that the user aspirates, and therefore subsequently dispenses, an incorrect dose—too much or too little—of the drug, thus making undesired dosing errors. An overdose of pharmaceutical product can in fact be harmful to health, whereas an underdose of the pharmaceutical product can reduce the efficacy thereof, thus slowing down the healing process. It follows that, during the step of aspirating the pharmaceutical product into the dosing syringe, the user must take great care so that the correct dose of pharmaceutical product is introduced into the hollow cylindrical body. An error in the correct dosing of the aspirated, and therefore dispensed, pharmaceutical product has the further consequence of the non-reproducibility of the dose, e.g., in cases in which the therapy envisages the administration of the same dose of pharmaceutical product various times a day and/or for various consecutive days.

To solve these problems, different solutions have been proposed.

A first solution consists of a ring, which is fitted onto the hollow cylindrical body and positioned by the user at a notch on the graduated scale related to the volume of drug that is to be aspirated/dispensed. During the sliding of the plunger within the hollow cylindrical body, a proximal end with a larger cross section of the plunger exercises pressure against the inner wall of the hollow cylindrical body, deforming it locally. When the proximal end with the larger cross section reaches the outer ring, the latter prevents the hollow cylindrical body from being deformed, thus blocking the stroke of the plunger.

This, extremely simple, solution has the drawback of not guaranteeing the repeatability of the dose. The ring fitted onto the hollow cylindrical body could, in fact, move accidentally, or even be removed, causing in the latter case the plunger to exit from the hollow cylindrical body and the consequent leaking of the pharmaceutical product from the dosing syringe.

It follows that the user, before aspirating the pharmaceutical product using such a dosing syringe, will have to check that the outer ring is correctly positioned at the desired notch of the graduated scale and this is disadvantageous as it complicates the use of the syringe, making it slower.

Such dosing syringe is also inconvenient to disassemble and reassemble, operations which are necessary during the washing of the syringe for removing product residues inside it.

Another known solution consists of obtaining, on the stem of the dosing syringe, a series of seats for housing an elastic ring. During use, the elastic ring is positioned in a seat corresponding to the volume of pharmaceutical product to be aspirated/dispensed. Following the sliding of the plunger within the hollow cylindrical body, the elastic ring abuts against a mechanical stop provided at a proximal end of the hollow cylindrical body, thus determining the aspiration into the syringe of the desired dose of pharmaceutical product.

Such second solution, although effective, is not functional. In fact, whenever the user wishes to vary the dose of pharmaceutical product to be aspirated/dispensed with the dosing syringe, he must necessarily disassemble the syringe, i.e., extract the plunger from the hollow cylindrical body, disengage the ring from the seat in which it is housed and position it in the seat corresponding to the new volume to be aspirated/dispensed. Furthermore, the volume of pharmaceutical product that can be aspirated/dispensed is dictated by the distance between the seats and cannot therefore be varied continuously.

Another known solution consists of forming a plurality of channels in the plunger, which extend between a fixed stop, provided at a distal end of the hollow cylindrical body, and corresponding stops provided in the plunger, longitudinally to the plunger. The length of each channel, provided by the distance between its stop and the fixed stop of the hollow cylindrical body, determines a corresponding dosing volume.

This further known solution has, like the previous one, the disadvantage of enabling the aspiration of only predetermined and unmodifiable volumes of pharmaceutical product. Furthermore, it has a complex structure, which complicates the disassembly and reassembly thereof, which are necessary for internal cleaning. Finally, another disadvantage is that also in this case the user must check that the setting of the volume of pharmaceutical product to be aspirated is correct, as this setting may be changed accidentally when the dosing syringe is not being used.

SUMMARY

The main object of the present invention is therefore that of making available a dosing syringe that can overcome the drawbacks mentioned above with reference to dosing syringes of the known type.

More in particular, the main object of the present invention is that of making available a dosing syringe configured so as to be able to vary in a continuous, controlled, and repeatable way the dose of pharmaceutical product aspirated and/or dispensed and to be able to fix the chosen dose for subsequent aspirations to the first.

Yet another object of the present invention is that of making available a dosing syringe configured so as to prevent accidental variation of the volume of pharmaceutical product to be aspirated and/or to be dispensed, set previously by a user.

Yet another object of the present invention is that of making available a dosing syringe configured so as to be able to be easily disassembled, in order to be washed, both internally and externally.

Yet another object of the present invention is that of facilitating the user in the operation of fixing the dose to be aspirated and/or dispensed.

Yet another object of the present invention is that of making available a dosing syringe configured in order to enable the user to easily vary the predetermined dose of product to be aspirated, without it being necessary to dis-assemble the syringe.

Last but not least object of the present invention is that of making available a dosing syringe, which can be produced more quickly and cheaply with respect to the production of traditional dosing syringes, and that is also easy and imme-diate to use.

These and other objects, which will appear more clearly in the following description, are achieved by a dosing syringe according to the independent claim 1. Preferred characteristics of the dosing syringe are reported in the dependent claims from 2 to 12.

Therefore, the invention relates, in a first aspect thereof, to a dosing syringe comprising a hollow cylindrical body and a plunger slidable within the hollow cylindrical body.

The dosing syringe is characterized in that it further comprises at least one slider being slidable within a distal flange of the hollow cylindrical body, transversally to the hollow cylindrical body, and in that at least one wall is formed in the plunger for abutting and blocking the slider during its sliding within the flange, the at least one abutting and blocking wall providing a mechanical stop which stops the stroke of the plunger at a volume of product to be aspirated and/or dispensed.

The at least one abutting and blocking wall of the slider during its sliding within the flange is an inclined wall.

Such combination of features advantageously enables the volume of product to be aspirated and/or dispensed continu-ously and easily. Furthermore, once the dose of product to be dispensed has been set, such dose can be repeated precisely and without it being necessary to control it every time. The dosing syringe according to the invention can therefore be used also by a third party, as the predefined volume of product cannot be changed accidentally.

Again, thanks to the presence of at least one slider, the plunger cannot exit from the hollow cylindrical body, which would cause wasted product. Otherwise, to completely extract the plunger from the hollow cylindrical body, it is necessary for the user to first proceed to remove the at least one slider from the dosing syringe. The slider(s) therefore act(s), advantageously, as safety element(s), preventing any waste of pharmaceutical product in the event of a mistake during the aspiration thereof.

In the following of the present description, and in the attached claims, the term "proximal" indicates portions of the various components of the dosing syringe directed, during use, towards the body of a user of the product dispensed by the syringe, whereas the term "distal" indicates portions of the various components of the dosing syringe directed, during use, away from the body of a user of the product dispensed by the syringe.

BRIEF DESCRIPTION OF THE DRAWINGS

Further characteristics and advantages of the present invention will become clearer from the following detailed description of its preferred embodiments, given below, by way of non-limiting example, with reference to the attached drawings. In the drawings:

FIG. 21 (*b*) is a perspective view of a dosing syringe according to a fifth alternative embodiment of the present invention, in an operating position of the plunger and of the slider;

FIG. 21 (*c*) is a perspective view of a dosing syringe according to a fifth alternative embodiment of the present invention, in an operating position of the plunger and of the slider;

FIG. 21 (*d*) is a perspective view of a dosing syringe according to a fifth alternative embodiment of the present invention, in an operating position of the plunger and of the slider;

FIG. 21 (*e*) is a perspective view of a dosing syringe according to a fifth alternative embodiment of the present invention, in an operating position of the plunger and of the slider;

DETAILED DESCRIPTION OF THE EMBODIMENTS

With reference to FIGS. 1 to 7, a dosing syringe is illustrated therein according to a preferred embodiment of the present invention.

The dosing syringe, indicated in general by reference number 100, comprises a hollow cylindrical body 10, typically transparent, adapted to contain a volume of a product or pharmaceutical product to be dispensed, and a plunger 20 slidable within the hollow cylindrical body 10 for aspirating into the hollow cylindrical body 10, and subsequently dispensing from the hollow cylindrical body 10, the desired volume of product.

Figure 1:
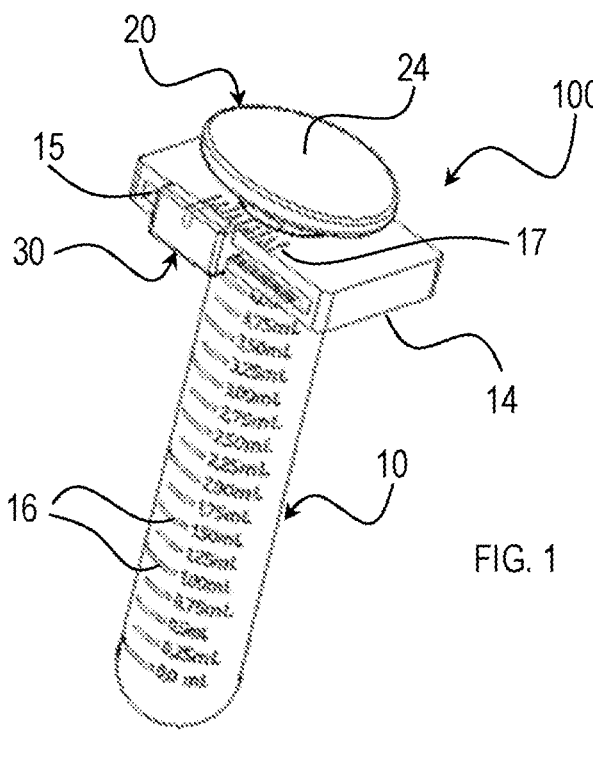
FIG. 1 is a perspective schematic view, not to scale, of a dosing syringe according to a first preferred embodiment of the present invention, with the plunger in the position completely inserted within the hollow cylindrical body.
Figure 2:
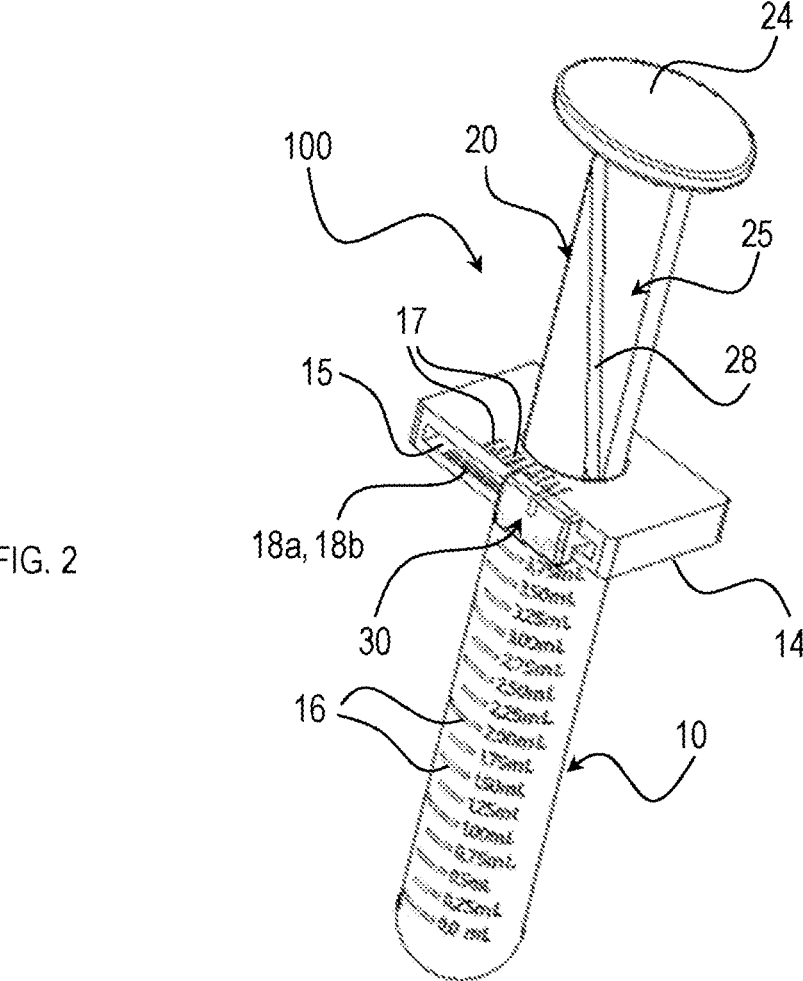
FIG. 2 is a perspective view of the dosing syringe of FIG. 1, with the plunger in the maximum extraction position from the hollow cylindrical body.
Figures 3, 4, 5:
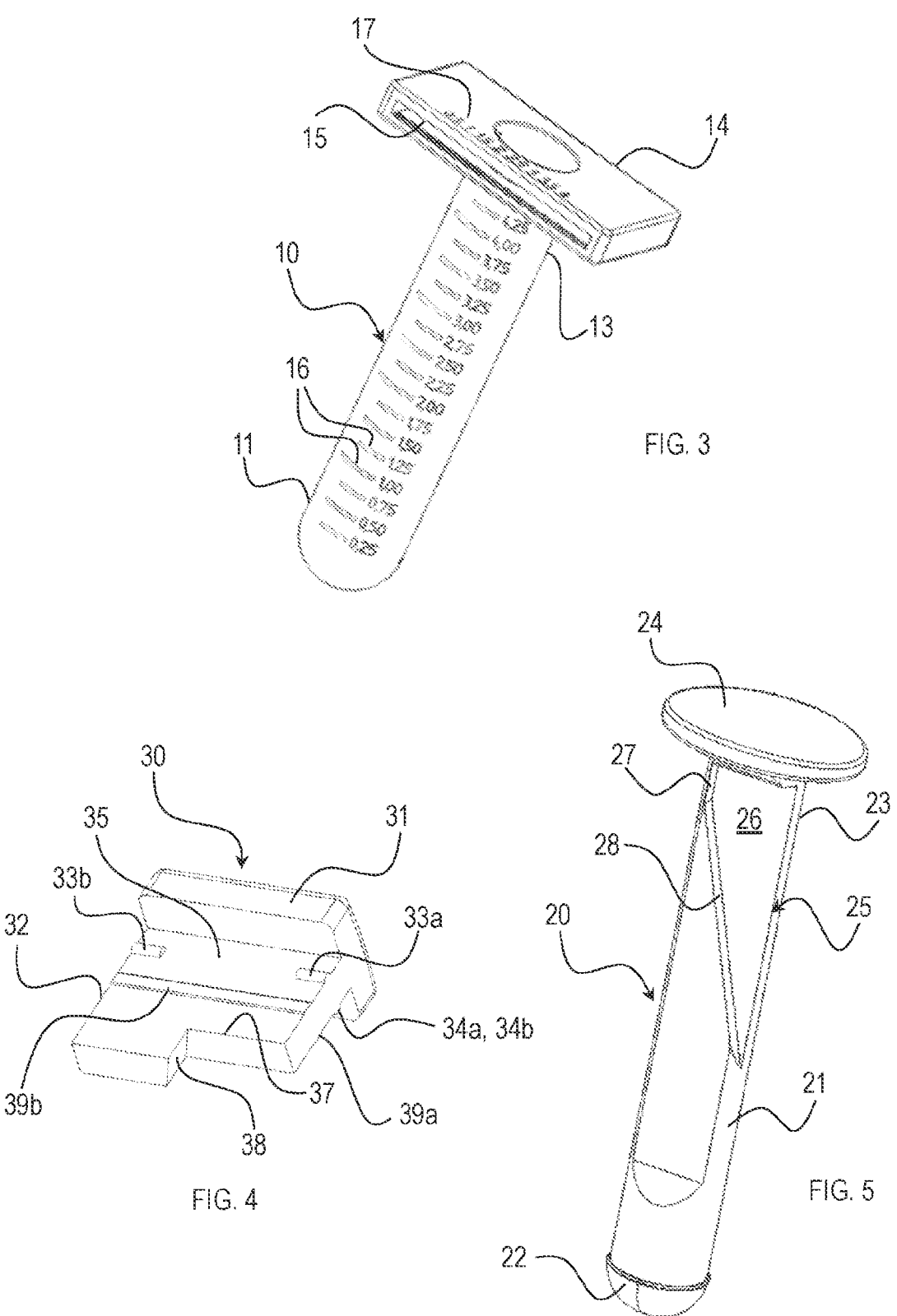
FIG. 3 is a perspective view of the hollow cylindrical body of the dosing syringe of FIG. 1.
FIG. 4 is a perspective view of the slider of the dosing syringe of FIG. 1.
FIG. 5 is a perspective view of the plunger of the dosing syringe of FIG. 1.
Figures 6, 7:
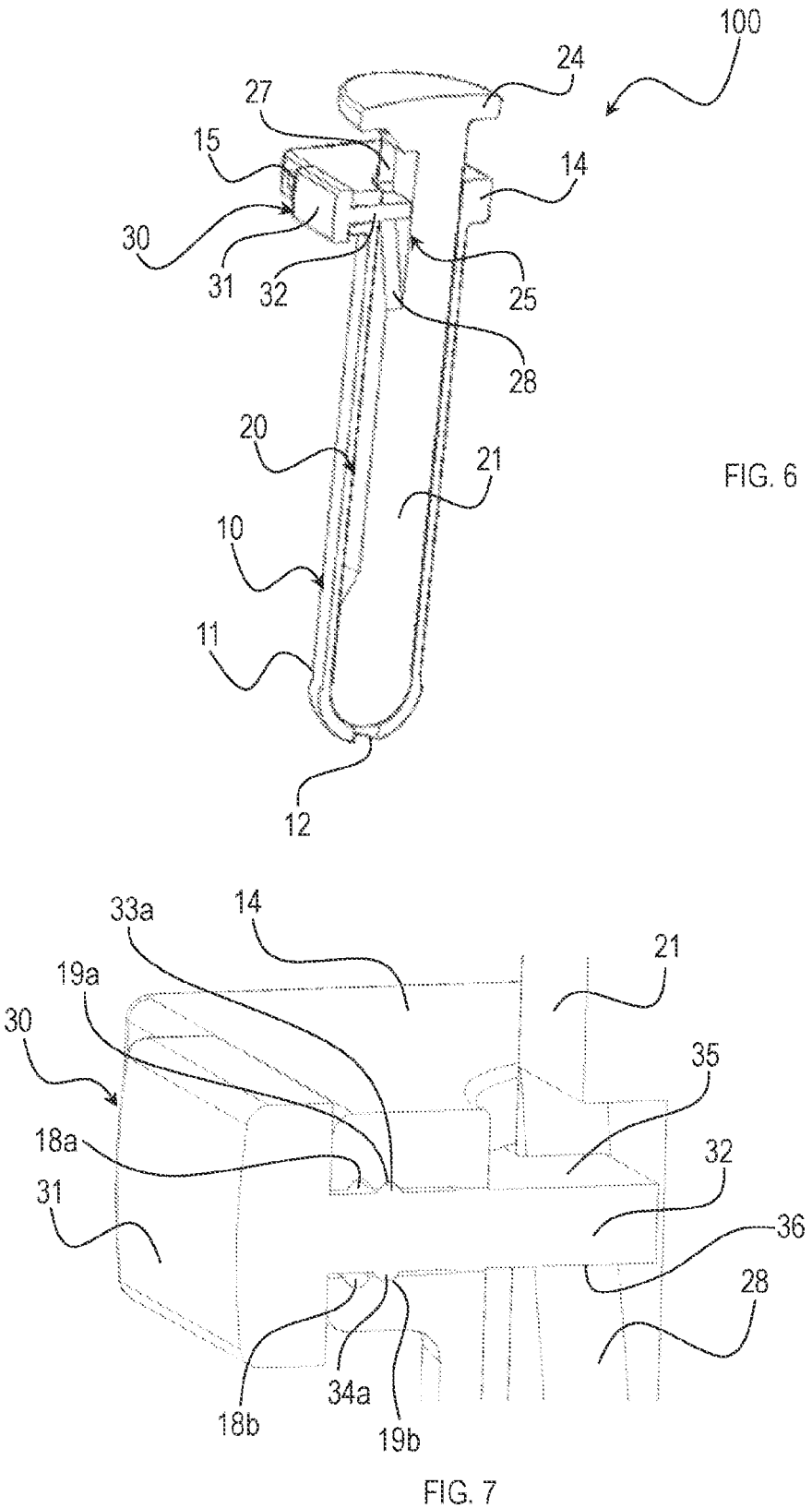
FIG. 6 is a longitudinal sectional perspective view of the dosing syringe of FIG. 1.
FIG. 7 is a partial view of a detail of FIG. 6, which shows the slider in its position blocked inside the flange of the syringe.
Figures 8, 9:
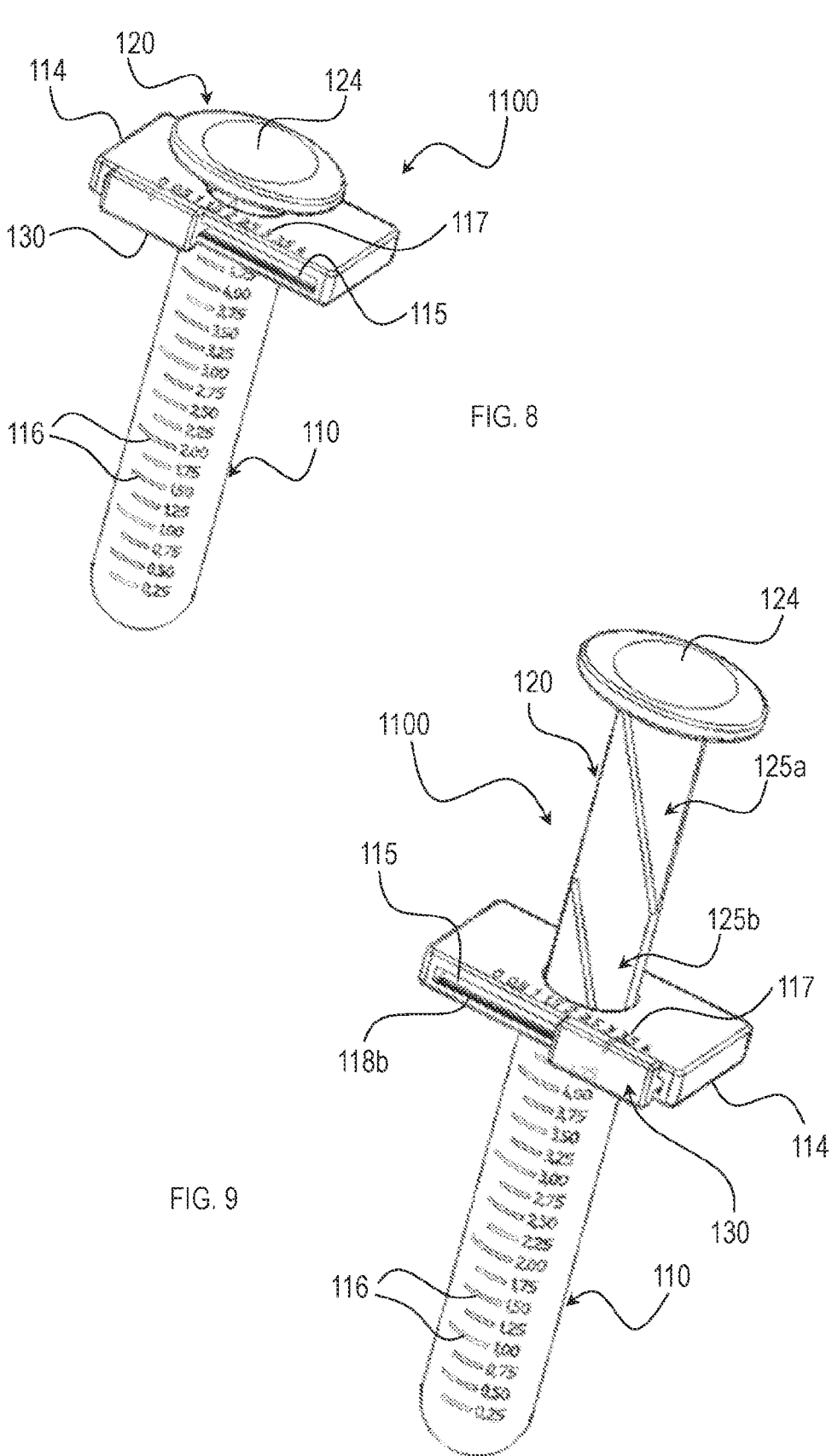
FIG. 8 is a perspective schematic view, not to scale, of a dosing syringe in compliance with a second alternative embodiment of the present invention, with the plunger in the position completely inside the hollow cylindrical body.
FIG. 9 is a perspective view of the dosing syringe of FIG. 8, with the plunger in the partially extracted position from the hollow cylindrical body.

As shown in detail in FIGS. 3 and 6, the hollow cylindrical body 10 has at a proximal end thereof 11, i.e., the end turned, during use, towards the body of a user of the product dispensed by the syringe, an aspiration/dispensing opening 12 of the product into/from the dosing syringe 100. At a distal end 13 thereof, i.e. the end turned, during use, away from the body of the user of the product dispensed by the syringe, the hollow cylindrical body 10 instead has a flange 14, preferably parallelepiped shaped, provided with a longitudinal slot 15 for the slidable housing of a slider 30, which moves transversally to the hollow cylindrical body 10 and, as will be described in more detail below, has the function of regulating and blocking the stroke of the plunger 20 within the hollow cylindrical body 10, in order to control the dose of product aspirated and/or dispensed into/from the dosing syringe 100. The flange 14 can be obtained as a single piece with the hollow cylindrical body 10 or be a separate piece and subsequently assembled immovably onto the hollow cylindrical body 10, during the step of manufacturing the dosing syringe 100.

On the hollow cylindrical body 10 a series of measurement notches 16 is provided, with each notch being accompanied by a number indicating the volume of product in millilitres. A corresponding series of measurement notches 17 is preferably also provided on the flange 14.

As shown in more detail in FIG. 5, the plunger 20 has an elongated body 21, a proximal end 22 of which, i.e., the end turned during use towards the body of a user of the product dispensed by the syringe, preferably has a cross section slightly larger than the internal cross section of the hollow cylindrical body 10. This advantageously enables the plunger 20, during its sliding within the hollow cylindrical body 10, to create a seal against an inner wall of the hollow cylindrical body 10, thus creating the necessary vacuum for the aspiration of the product from a vial or bottle that contains it, into the dosing syringe 100. Typically, the aspiration of the product from the vial or bottle to the dosing syringe takes place by means of an adapter (not shown) mounted on the proximal end 11 of the hollow cylindrical body 10 and subsequently engaged on the mouth of the vial or bottle.

At a distal end 23 thereof, i.e., the end turned, during use, away from the body of the user of the product dispensed by the syringe, the plunger 20 has a head 24 adapted to enable a user to grip the dosing syringe 100 and to exercise on the plunger 20 the necessary force to make it slide within the hollow cylindrical body 10, both during the aspiration step and during the dispensing of the product into/from the dosing syringe 100.

In the embodiment illustrated, the hollow cylindrical body 10 and the plunger 20 have an elliptical cross-section which advantageously prevents the plunger 20 from rotating within the hollow cylindrical body 10 during the step of setting the desired dose of pharmaceutical product to be aspirated and/or dispensed, as will be disclosed in more detail in the following present description.

A longitudinal recess 25 is formed in the elongated body 21 of the plunger 20, the recess comprising a bottom wall 26 and an edge, extending orthogonally to the bottom wall 26 and comprising an inclined portion 28 extending from the distal end 23, for the entire length of the plunger 20, so that the width of the longitudinal recess decreases moving from top to bottom and from left to right along the plunger 20.

The inclined portion 28 acts as an inclined abutting and blocking wall of the slider 30 during the sliding thereof within the longitudinal slot 15 of the flange 14 of the hollow cylindrical body 10, so as to create an actual mechanical abutment that stops the stroke of the plunger 20 at the desired volume or dose of aspirated product.

Preferably, the edge of the recess 25 has a straight portion 27, which extends immediately below the gripping head 24, between the distal end 23 and the inclined portion 28 to facilitate the grip of the plunger 20 by a user.

As shown in more detail in FIGS. 4 and 7, the slider 30 has a T-shaped configuration and comprises a first portion 31 and a second portion 32 extending orthogonally from the first portion 31. The first portion 31 projects from the longitudinal slot 15 of the flange 14 and the user can act on this to make the slider 30 slide transversally with respect to the hollow cylindrical body 10 and to lock it in position at the desired dose of product to be dispensed. The second portion 32 is instead housed within the longitudinal slot 15, which can slide and be blocked inside it.

To enable the transversal and rectilinear sliding of the slider 30 within the flange 14 of the hollow cylindrical body 10, longitudinal ribs are formed at the second portion 32 of the slider 30. In particular, the longitudinal ribs comprise two opposing pairs of longitudinal ribs 33*a*, 33*b* and 34*a*, 34*b*, each pair being obtained on a respective upper and lower surface, 35, 36 of the second portion 32 of the slider, the ribs 33*a*, 33*b* and 34*a*, 34*b* of each pair being aligned with one another and formed at peripheral portions of the upper surface 35 and of the lower surface 36.

The longitudinal ribs 33a, 33b and 34a, 34b are configured to slide within corresponding grooves 18a, 18b, also longitudinal and parallel to one another, formed at opposing surfaces of the longitudinal slot 15 of the flange 14 of the hollow cylindrical body 10. Preferably, the longitudinal ribs 33a, 33b and 34a, 34b and the respective sliding grooves 18a, 18b are complementary, the sliding grooves 18a, 18b having a slightly larger shape than that of the longitudinal ribs 33a, 33b and 34a, 34b, so that there is a certain clearance between grooves and ribs.

At the opposing surfaces of the longitudinal slot 15, further grooves 19a, 19b are also formed, each groove being parallel to a corresponding sliding groove 18a, 18b of the slider 30 and more recessed with respect thereto in the radial direction.

The further grooves 19a, 19b are used to block the slider 30 in position, thus preventing any further sliding within the slot 15 of the flange 14. For that purpose, the blocking grooves 19a, 19b have a complementary and smaller shape than that of the longitudinal grooves 33a, 33b and 34a, 34b, so that each longitudinal rib 33a, 33b and 34a, 34b can be engaged in a snap-fit way, i.e., without any clearance, into the respective blocking groove 19a, 19b.

The additional grooves 19a, 19b are also configured so as to produce a "click", which acoustically signals to the user of the syringe that the slider is blocked in position within the syringe and therefore the dose of product to be aspirated and/or dispensed has been correctly fixed.

Naturally, and without departing from the scope of the present invention, instead of two opposing and symmetrical pairs of longitudinal ribs, it is possible to envisage only one pair of aligned ribs formed on the upper or lower surface of the slider, or a pair of facing ribs, each formed on a respective, upper and lower, surface of the slider. Again, the pair(s) of peripheral ribs can be substituted by ribs extending for the entire length of the slider.

Figure 22:
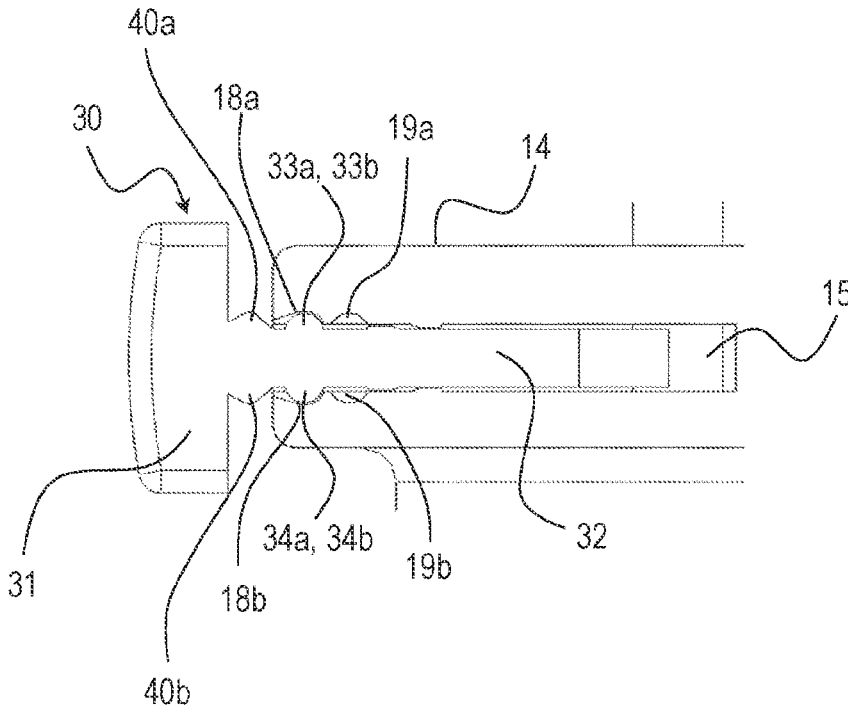
FIG. 22 is a partial lateral, sectional view, to enlarged scale, of a variant of the slider, in the disengaged, or sliding, position within the flange of the dosing syringe.
Figure 23:
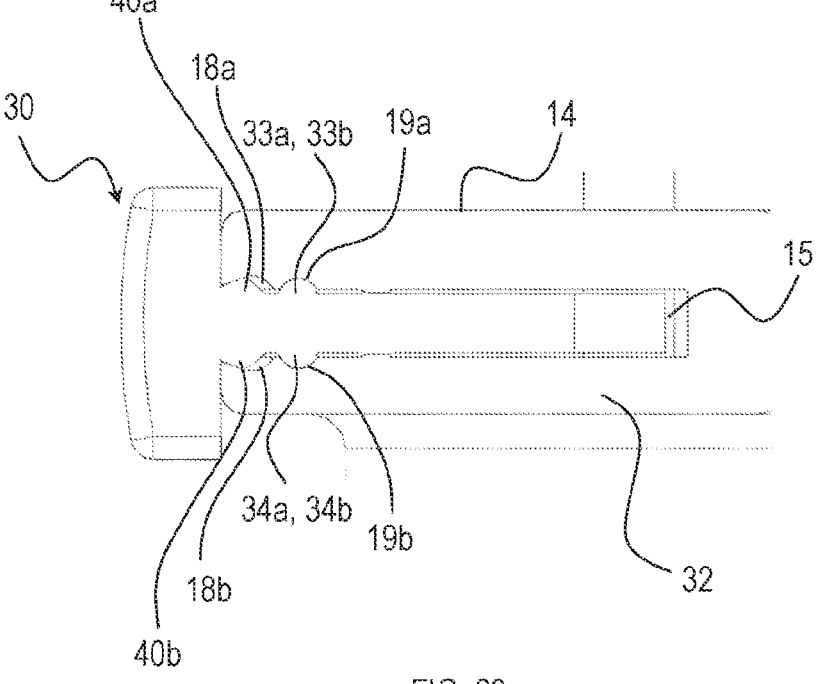
FIG. 23 is a partial lateral, sectional view, to enlarged scale, of a variant of the slider, respectively in the engaged, or blocking, position, within the flange of the dosing syringe.

As a further different embodiment of the slider according to the invention, FIGS. 22 and 23 illustrate a slider 30, which comprises additional longitudinal ribs 40a, 40b, also formed on the first position 31 such for which, when the slider 30 is in its disengaged position, i.e., sliding within the flange 14, they are external to the flange (FIG. 22). Correspondingly, the longitudinal ribs 33a, 33b and 34a, 34b are housed with clearance in the sliding grooves 18a, 18b. When the slider 30 is blocked in position within the flange 14, the additional longitudinal ribs 40a, 40b are housed in a snap-fit way within the longitudinal grooves 18a, 18b (FIG. 23) and the longitudinal ribs 33a, 33b and 34a, 34b are engaged in a snap-fit way into the blocking grooves 19a, 19b. Naturally, the additional longitudinal ribs 40a, 40b have a slightly larger dimension than that of the sliding grooves 18a, 18b, so as to be able to be engaged in a snap-fit way, i.e. without any clearance, therein. Such a configuration of the slider 30 advantageously enables better blocking of the slider 30 in the syringe and therefore better control of the product dose to be aspirated and/or dispensed.

Preferably, at the upper and lower surface 35 and 36 of the second portion 32 of the slider, longitudinal reliefs 39a, 39b are formed, which advantageously promote the maintenance of the slider 30 in its position blocked within the flange 14, further preventing the uncoupling between the longitudinal ribs 33a, 33b and 34a, 34b and the respective blocking grooves 19a, 19b.

The second portion 32 of the slider 30 preferably has, at a free end thereof, an undercut 37, which defines a surface 38 adapted to abut, in use, against the abutting and blocking wall 28 of the slider 30, as will be explained in more detail in the following of the present description.

With reference to FIGS. 8 to 14, they illustrate a dosing syringe in compliance with a second embodiment of the present invention, which differs from the one described above and illustrated in FIGS. 1 to 7 due to the fact that it comprises, instead of only one longitudinal recess, a pair of longitudinal recesses, each of which delimits a respective abutting and blocking wall of the slider during the sliding thereof within the dosing syringe, creating a respective mechanical abutment that stops the stroke of the plunger at the volume or desired dose of product.

Such a configuration of the plunger advantageously enables the quantity of product that can be aspirated/dispensed within the syringe to be increased, e.g., up to a maximum of 5 ml-6 ml of aspirated/dispensed product.

The dosing syringe, indicated in general by reference number 1100, therefore comprises a hollow cylindrical body 110, typically transparent and on which a series of measurement notches 116 is preferably provided, adapted to contain a volume of product or pharmaceutical product to be dispensed, and a plunger 120 slidable within the hollow cylindrical body 110.

The hollow cylindrical body 110 has, at a proximal end 111 thereof, an opening 112 (see FIG. 14) for the aspiration/dispensing of the product into/from the dosing syringe 1100, whereas, at a distal end 113 thereof, a flange is formed, preferably having a parallelepiped shape 114, provided with a longitudinal slot 115 for the slidable housing of a slider 130 having the function of regulating and blocking the stroke of the plunger 120 within the hollow cylindrical body 110, in order to control the quantity of product aspirated and/or dispensed into/from the dosing syringe 1100. On the flange, a series of measurement notches 117 is preferably provided, corresponding to those present on the hollow cylindrical body 110.

The plunger 120 has, at a distal end 123 thereof a gripping head 124, whereas a proximal end 122 of the plunger 120 preferably has a cross section slightly larger than the internal cross section of the hollow cylindrical body 110; this is in order to enable the necessary vacuum to be created for the aspiration of the product from a vial or bottle that contains it into the dosing syringe 1100.

In the embodiment illustrated, the hollow cylindrical body 110 and the plunger 120 have an elliptical cross section.

Figures 10, 11, 12:
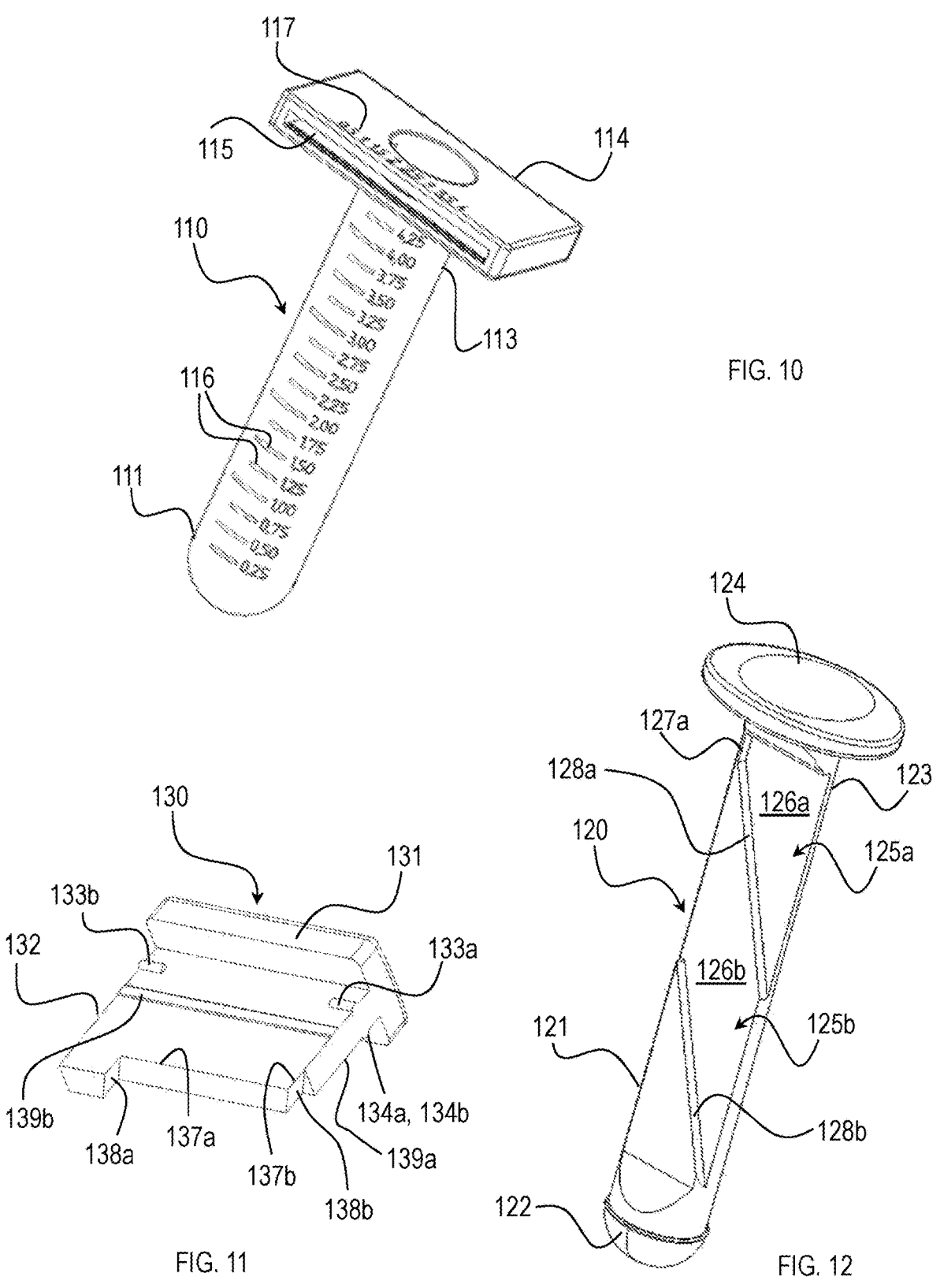
FIG. 10 is a perspective view of the hollow cylindrical body of the dosing syringe of FIG. 8.
FIG. 11 is an enlarged perspective view of the slider of the dosing syringe of FIG. 8.
FIG. 12 is a perspective view of the plunger of the dosing syringe of FIG. 8.
Figures 13, 14:
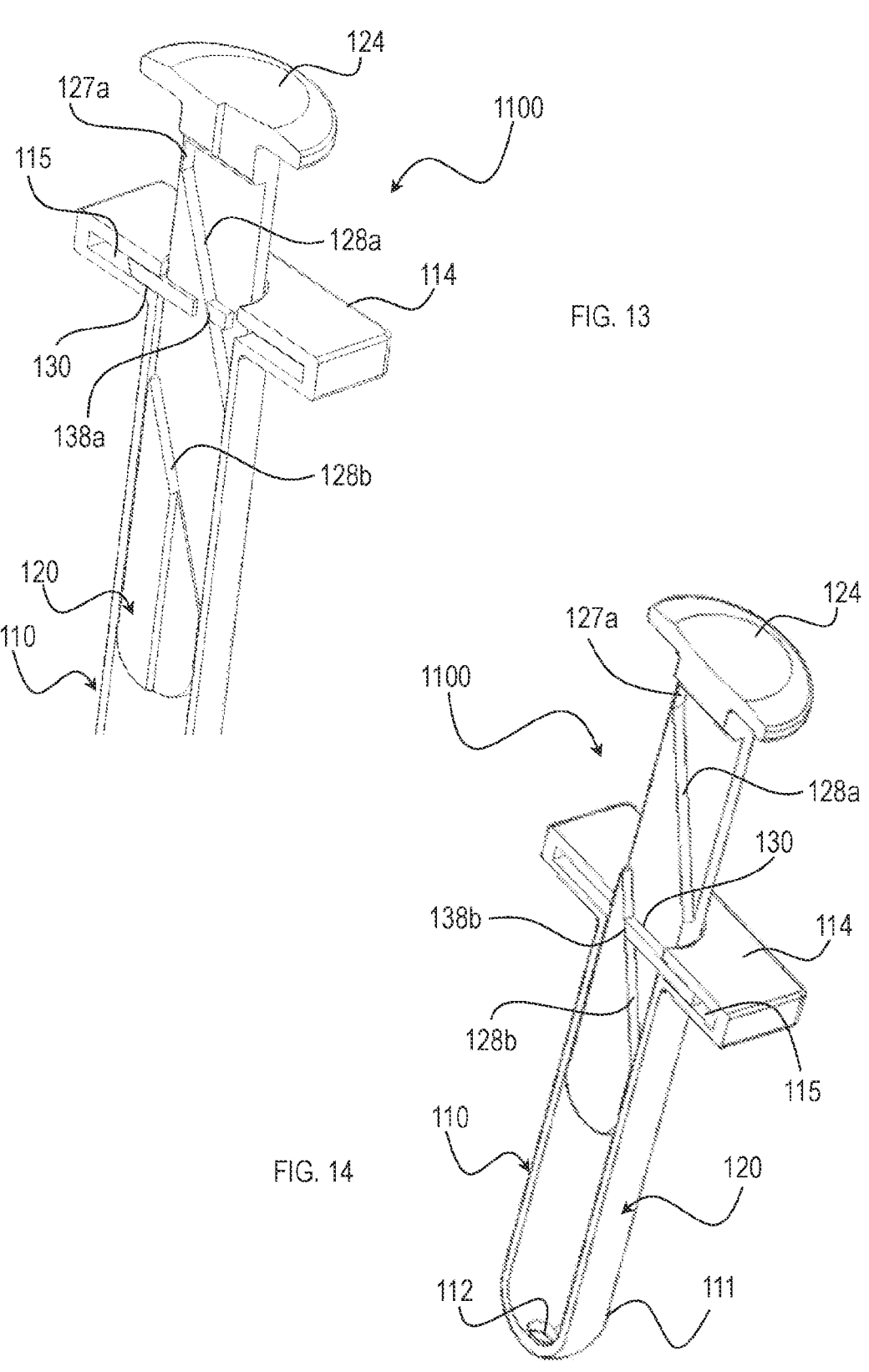
FIG. 13 is a perspective, sectional, and partial view of the dosing syringe of FIG. 8, with the plunger in a first operating or aspiration position of a first desired volume of pharma-ceutical product.
FIG. 14 is a perspective, section view of the dosing syringe of FIG. 8, with the plunger in a second operating or aspiration position of a second desired volume of pharma-ceutical product, greater than the first volume.

As shown in detail in FIG. 12, in the plunger 120 a pair of longitudinal recesses 125a, 125b is formed, i.e., a distal longitudinal recess 125a and a proximal longitudinal recess 125b, each of which comprises a bottom wall 126a, 126b and an edge, extending orthogonally to the bottom wall 126a, 126b and comprising and inclined portion 128a, 128b. Each inclined portion 128a, 128b preferably extends along the entire width of the plunger 120, so that the width of each longitudinal recess 125a, 125b decreases moving from top to bottom and from left to right along the plunger 120.

The longitudinal recesses 125a, 125b have different depths, e.g., the distal longitudinal recess 125a is deeper than the proximal longitudinal recess 125b.

The inclined portions 128a, 128b, preferably parallel to one another, act as an abutting wall of the slider 130 during its sliding within the longitudinal slot 115 of the flange 114 of the hollow cylindrical body 110, in order to create an actual mechanical abutment that stops the stroke of the plunger 120 at the desired volume of aspirated product.

More in particular, purely by way of example, the inclined portion 128a of the distal longitudinal recess 125a acts as an abutting wall of the slider 130 for the aspiration/dispensing of a maximum volume of product equal to about 2.5 ml-3 ml, whereas the inclined portion 128*b* of the proximal longitudinal recess 125*b* acts as an abutting wall of the slider 130 for the aspiration/dispensing of a maximum volume of product equal to about 5 ml-6 ml.

As a function of the maximum volume of product to be aspirated/dispensed, the slider 130 abuts on the inclined portion 128*a* of the distal longitudinal recess 125*a* or on the inclined portion 128*b* of the proximal longitudinal recess 125*b*.

Preferably, the edge of the longitudinal distal recess 125*a* also has a straight portion 127*a*, which extends immediately below the gripping head 124, between the distal end 123 and the inclined portion 128*a* to facilitate the grip of the plunger by a user.

With reference to FIG. 11, the slider 130, like the slider 30, has a T-shaped configuration and comprises a first portion 131 and a second portion 132 extending orthogonally from the first portion 131. The first portion 131 projects from the longitudinal slot 115 of the flange 114 and the user can act on this to make the slider 130 slide transversally with respect to the hollow cylindrical body 110 and to lock it in position at the dose of product to be dispensed. The second portion 132 is instead housed in the longitudinal slot 115 and slidable and blockable therein.

To enable the transversal and rectilinear sliding of the slider 130 within the flange 114 of the hollow cylindrical body 110, longitudinal ribs 133*a*, 133*b* e 134*a*, 134*b*, are obtained at the second portion 132 of the slider 130, which are configured to slide in corresponding grooves 118*a*, 118*b* formed at the opposing surfaces of the slot 115 of the flange 114 of the hollow cylindrical body 110. The longitudinal ribs 133*a*, 133*b* and 134*a*, 134*b* and the grooves 118*a*, 118*b* are exactly the same as the longitudinal ribs 33*a*, 33*b* and 34*a*, 34*b* and the grooves 18*a*, 18*b* of the dosing syringe 100 and therefore shall not be described further herein.

At the opposing surfaces of the slot 115 further grooves (not shown) are formed for blocking the slider 130 in position, which are very similar to the grooves 19*a*, 19*b* of the slider 30 and therefore they are not described further herein.

Preferably, the slider 130 has longitudinal reliefs 139*a*, 139*b*, which advantageously promote the maintenance of the slider 130 in the blocked position thereof within the flange 114, further preventing the uncoupling between the longitudinal ribs 133*a*, 133*b* and 134*a*, 134*b* and the respective blocking grooves.

Unlike the slider 30, the second portion 132 of the slider 130 has, at a free end thereof, not one but a pair of undercuts 137*a*, 137*b*, each of which defines a surface 138*a*, 138*b* intended to abut, in use, against the corresponding abutting wall 128*a*, 128*b* of the plunger 120, as will be explained in more detail in the following of the present description.

In particular, the abutting surfaces 138*a* and 138*b* of the undercuts 137*a*, 137*b* are placed at two different distances from the first portion 131 of the slider. It follows that when, as will be described in detail below, the slider 130 is pressed against the flange 114 for blocking it in position, only one of the two abutting surfaces 138*a* and 138*b* is abutted against the corresponding inclined portion 128*a*, 128*b* of the plunger 120. Therefore, interferences in the sliding and locking in position movements of the slider 130 are advantageously prevented.

Figures 15, 16:
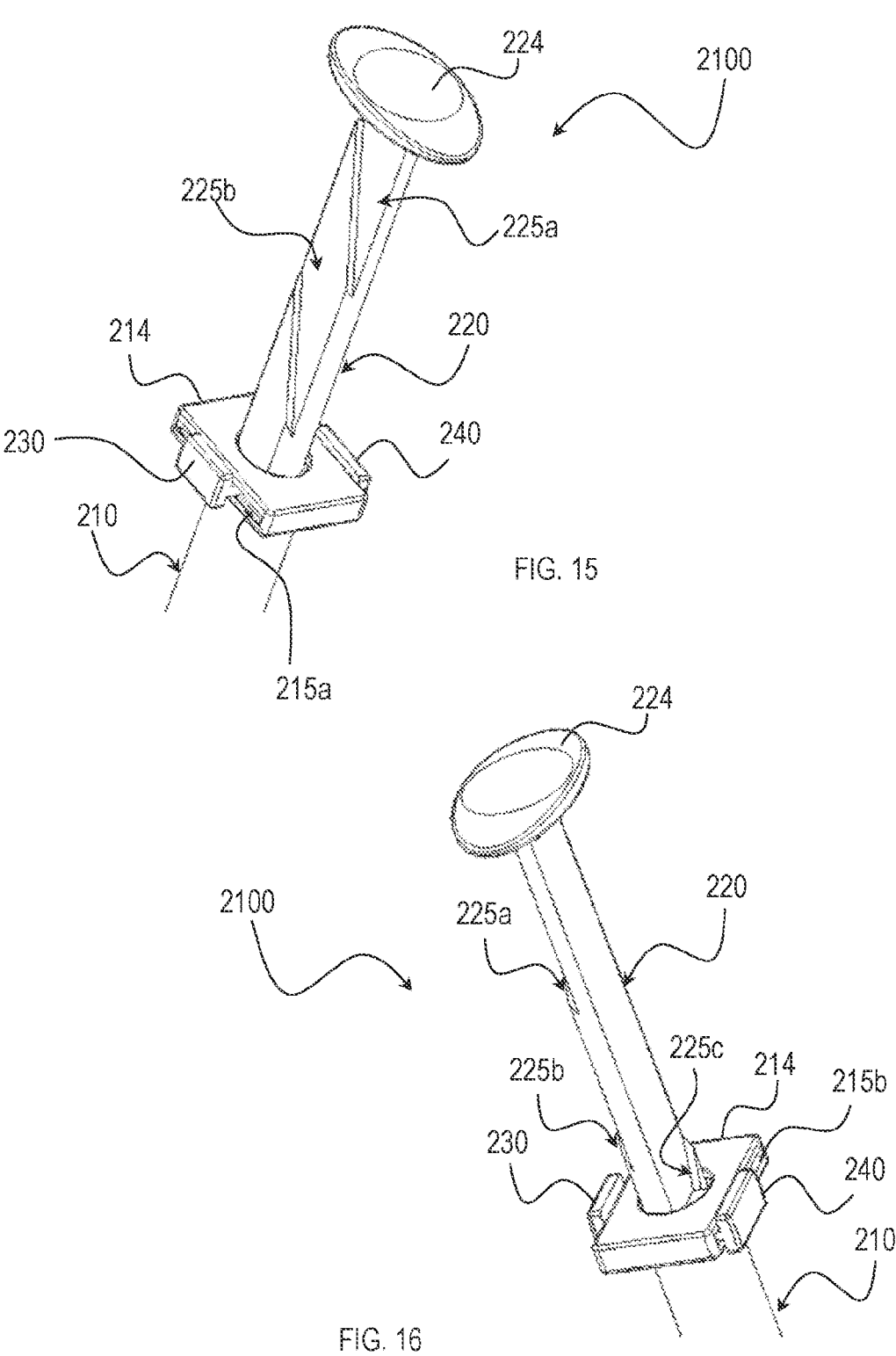
FIG. 15 is a partial perspective view of a dosing syringe according to a third alternative embodiment of the present invention.
FIG. 16 is a partial perspective view, taken from a different angle, of the dosing syringe of FIG. 15.

FIGS. 15 and 16 show a dosing syringe according to a third embodiment of the present invention, which differs from the one described above and illustrated in FIGS. 8 to

14 in that it comprises one or more additional longitudinal recesses and a second slider that can be engaged with such recesses, in an opposing position with respect to the first slider.

The dosing syringe, indicated in general with reference number 2100, therefore comprises a hollow cylindrical body 210 and a plunger 220 provided with a gripping head 224 and slidable within the hollow cylindrical body 210.

The hollow cylindrical body 210 has a flange 214, preferably parallelepiped shaped, provided with a pair of longitudinal slots 215*a*, 215*b*, arranged on opposite sides of the flange 214, each slidably housing a respective slider 230, 240 within it. Each slider 230, 240 has the function of blocking the stroke of the plunger 220 within the hollow cylindrical body 210, so as to control the quantity of product aspirated and/or dispensed into/from the dosing syringe 2100. The sliders 230 and 240 are very similar to the slider, and therefore shall not be described further herein.

In the embodiment illustrated, the hollow cylindrical body 210 and the plunger 220 have an elliptical cross section.

In the plunger 220 a pair of longitudinal recesses 225*a*, 225*b* is formed, very similar to the longitudinal recesses 125*a*, 125*b* of the dosing syringe 1100, to which reference is made. The plunger 220 has a further longitudinal recess 225*c* arranged on the opposite side with respect to the longitudinal recesses 225*a*, 225*b*. The further recess is the same as the longitudinal recesses 125*a*, 125*b* of the dosing syringe 1100 and will not therefore be described further herein.

A dosing syringe according to this third embodiment advantageously enables the volume of the product that can be aspirated and dispensed to be further increased, for example up to a maximum of 10 ml-12.5 ml.

As a further variant, it is possible to provide two pairs of opposing longitudinal recesses, for a total of four longitudinal recesses. Each longitudinal recess enables 2.5 ml-3.0 ml of product to be aspirated and dispensed, therefore, if it is necessary to dispense up to 9 ml of product, three longitudinal recesses and two sliders are provided; if, instead, it is necessary to dispense up to 12 ml of product, four longitudinal recesses and two sliders are provided.

Figure 17:
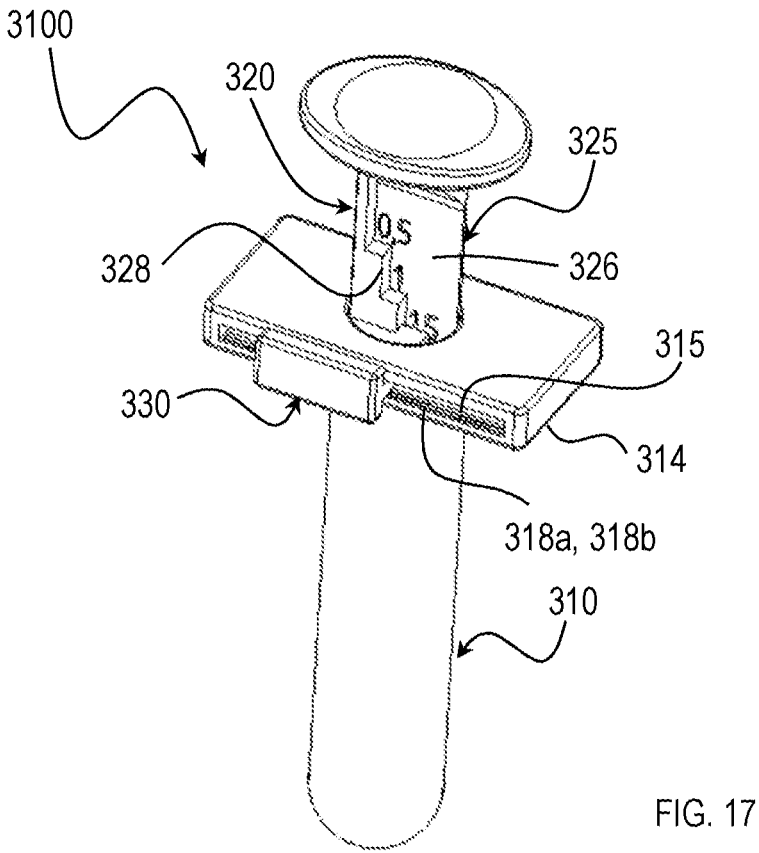
FIG. 17 is a perspective view of a dosing syringe accord-ing to a fourth alternative embodiment of the present inven-tion.
Figure 18:
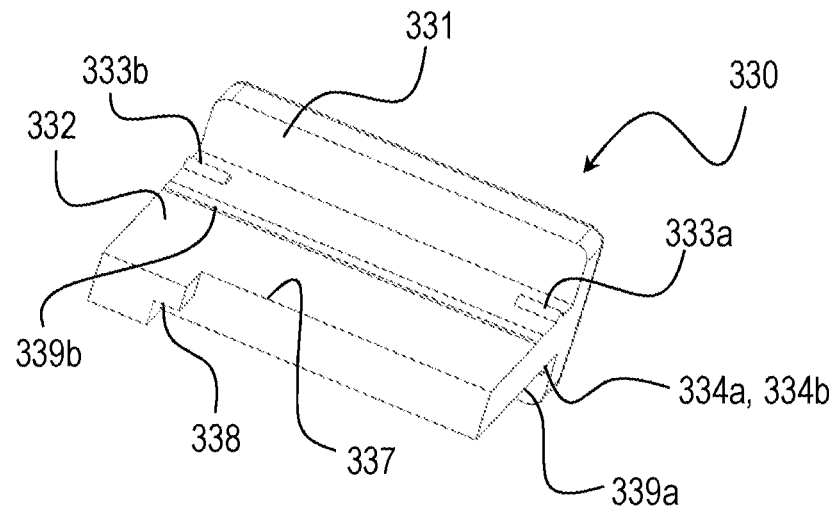
FIG. 18 is a perspective view, to an enlarged scale, of a slider of the dosing syringe of FIG. 17.

FIGS. 17 and 18 illustrate a dosing syringe according to a fourth embodiment of the present invention.

Such dosing syringe, indicated in general by reference number 3100, differs from the dosing syringes 100, 1100 and 2100 described above in terms of the different configuration of the abutting and blocking wall of the plunger which, instead of being uniform, has a stepped profile.

The dosing syringe 3100 therefore has a hollow cylindrical body 310, adapted to contain a volume of product or pharmaceutical product to be dispensed, and a plunger 320 slidable within the hollow cylindrical body 310.

In the embodiment illustrated, the hollow cylindrical body 310 and the plunger 320 have an elliptical cross section.

The hollow cylindrical body 310 has a flange 314 provided with a longitudinal slot 315 for the slidable housing of a slider 330, having the function of blocking the stroke of the plunger 320 within the hollow cylindrical body 310, in order to control the quantity of product to be aspirated and/or dispensed into/from the dosing syringe 3100.

In the plunger 320 a longitudinal recess 325 is formed, comprising a bottom wall 326 and an edge, extending orthogonally to the bottom surface 326 and comprising an inclined portion 328 preferably extending for the entire width of the plunger 320.

The inclined portion 328 has a stepped profile and acts as an abutting wall of the slider 330 during its sliding within the longitudinal slot 315 of the flange 314 of the hollow cylindrical body 310, in order to create an actual mechanical abutment that stops the stroke of the plunger 320 at the desired volume of aspirated product.

More in particular, each step of the inclined portion 328 acts as an abutting wall of the slider 330 for the aspiration/dispensing of predefined quantities of the product. At each step of the inclined stepped portion 328 there is a number indicating the volume of product in millilitres. The numbers displayed at the steps correspond to a series of measurement notches (not shown) reported on the hollow cylindrical body 310. Naturally, it is possible to provide any number of steps as a function of the dosing precision to be obtained.

The slider 330, like the slider 30, has a T-shaped configuration and comprises a first portion 331, which projects from the longitudinal slot 315 of the flange 314 so that a user, by acting on it, can make the slider 330 slide transversally with respect to the hollow cylindrical body 310, and a second portion 332 extending orthogonally from the first portion 331 and housed slidably in the longitudinal slot 315.

To enable the transversal and rectilinear sliding of the slider 330 within the flange 314 of the hollow cylindrical body 310, longitudinal ribs 333a, 333b and 334a, 334b, are obtained at the second portion 332 of the slider 330, which are configured to slide in corresponding grooves 318a, 318b formed at the opposing surfaces of the longitudinal slot 315 of the flange 314 of the hollow cylindrical body 310. The longitudinal ribs 333a, 333b and 334a, 334b and the grooves 318a, 318b are exactly the same as the longitudinal ribs 33a, 33b and 34a, 34b and the grooves 18a, 18b of the dosing syringe 100 and therefore shall not be described further herein.

At the opposing surfaces of the slot 315 further grooves (not shown) are formed for blocking the slider 330 in position, very similar to the grooves 19a, 19b of the slider 30 and therefore not described further herein.

Preferably, the slider 330 has longitudinal reliefs 339a, 339b, which advantageously promote the maintenance of the slider 330 in the blocked position thereof within the flange 314, further preventing the uncoupling between the longitudinal ribs 333a, 333b and 334a, 334b and the respective blocking grooves.

Unlike the slider 30, the second portion 332 of the slider 330 has, at a free end thereof, an undercut 337, which defines a stepped surface 338 intended to abut, in use, against a corresponding step of the stepped abutting wall 328 of the plunger 320. Naturally, it is possible to provide various stepped surfaces according to the dosing precision to be obtained.

With reference to FIGS. 6, 7 and 13, 14, the operation of the dosing syringes 100 and 1100 described above will now be illustrated. Naturally, what is described below with reference to the dosing syringes 100 and 1100 is also valid for the dosing syringe 2100, which differs from the dosing syringe 1100 in terms of the different number of longitudinal recesses formed in the plunger.

It is therefore assumed that a user wishes to dispense a predetermined, controlled, and repeatable quantity of a product, e.g., a syrup to be administered to a child.

For that purpose, the dosing syringe 100, 1100 is coupled to a bottle containing the syrup, typically by the interposition of an adapter (not shown), and the user, by acting on the gripping head 24, 124, makes the plunger 20, 120 slide within the hollow cylindrical body 10, 110 until positioning the proximal end 22, 122 of the plunger 20, 120 at the notch 16, 116 indicating the desired dose in millilitres.

At this point, the user, by acting on the first portion 31, 131, makes the slider 30, 130 slide, which is in its disengaged or sliding position, i.e. with the longitudinal ribs 33a, 33b, 133a, 133b and 34a, 34b, 134a, 134b housed in the sliding grooves 18a, 18b, 118a, 118b, within the longitudinal slot 15, 151 of the flange 14, 141, until bringing the abutting surface 38, 138a, 138b of the undercut 37, 137a, 137b in abutment against the inclined portion 28, 128a, 128b of the edge of the longitudinal recess 25, 125a, 125b formed in the plunger 20, 120.

The user can at this point block the slider 30, 130 in position.

For that purpose, still acting on the first portion 31, 131, the user pushes the slider 30, 130 towards the inside of the longitudinal slot 15, 115, therefore orthogonally to the sliding direction, and following such thrust, the longitudinal ribs 33a, 33b, 133a, 133b and 34a, 34b, 134a, 134b are disengaged from the sliding grooves 18a, 18b, 118a, 118b, becoming inserted in a snap-fit way in the blocking grooves 19a, 19b, 119a, 119b. The quantity of aspirated product can therefore be dispensed.

Thanks to this configuration, the slider 30, 130 remains blocked in position and it is not possible to cause accidental unlocking. It follows that the user can aspirate, and subsequently dispense, always the same volume of product, therefore the dosing is controlled and repeatable. In fact, as long as the slider 30, 130 remains in its blocked position, each time it performs its product aspiration stroke, the plunger 20, 120, in particular the abutting wall 28, 128a, 128b thereof, abuts against the abutting surface of the slider at the product volume previously set.

Whenever the user wishes, instead, to set a different volume of product to be aspirated/dispensed, he/she must push the first portion 31, 131 of the slider 30, 130 outwards, so that the longitudinal ribs 33a, 33b, 133a, 133b and 34a, 34b, 134a, 134b are unconstrained from the blocking grooves 19a, 19b, 119a, 119b and repositioned in the sliding grooves 18a, 18b, 118a, 118b.

Whenever the dosing syringe 3100 shown in FIGS. 17 and 18 is used, the operation is very similar, with the sole difference that the slider 330 finishes its stroke when the stepped abutting surface 337 of the undercut 336 abuts against a corresponding step of the stepped inclined portion 328 of the longitudinal recess 325 formed in the plunger 320.

It follows that the dosing syringes described above, as well as guaranteeing that the user aspirates, and subsequently dispenses, the desired volume of product in a controlled and repeatable way, enable the volume of product aspirated and dispensed to be varied easily and with continuity.

Alternatively, it is possible to block the slider 30, 130 in position at the notches 17, 117 provided on the flange 14, 114 of the hollow cylindrical body 10, 110, according to the method described above, and therefore to act on the plunger 20, 120 for aspirating/dispensing the product.

Figure 19:
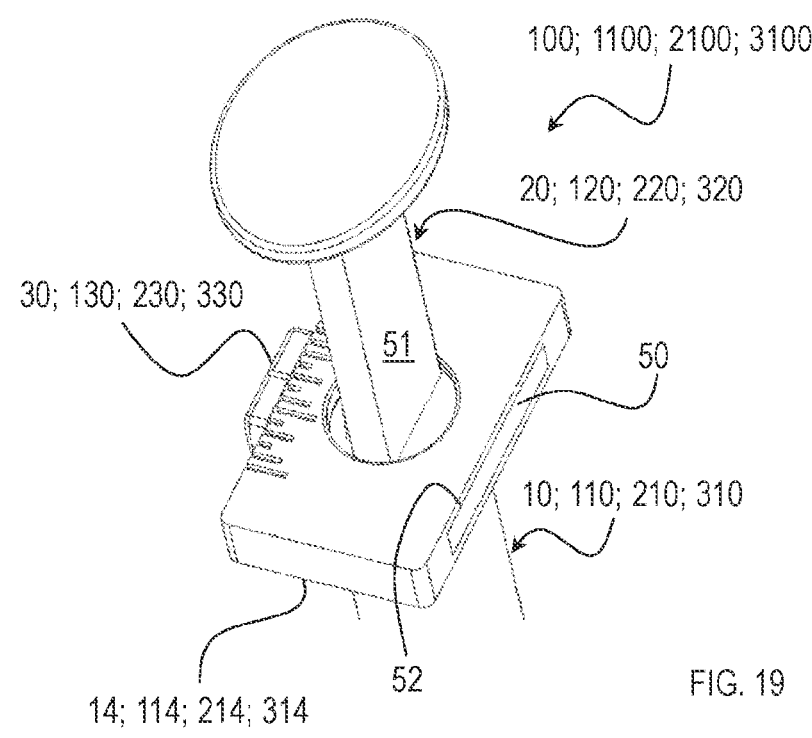
FIG. 19 is a partial perspective view of a dosing syringe according to the invention, which shows an anti-rotation element of the plunger with respect to the hollow cylindrical body, housed in the flange of the hollow cylindrical body.
Figure 20:
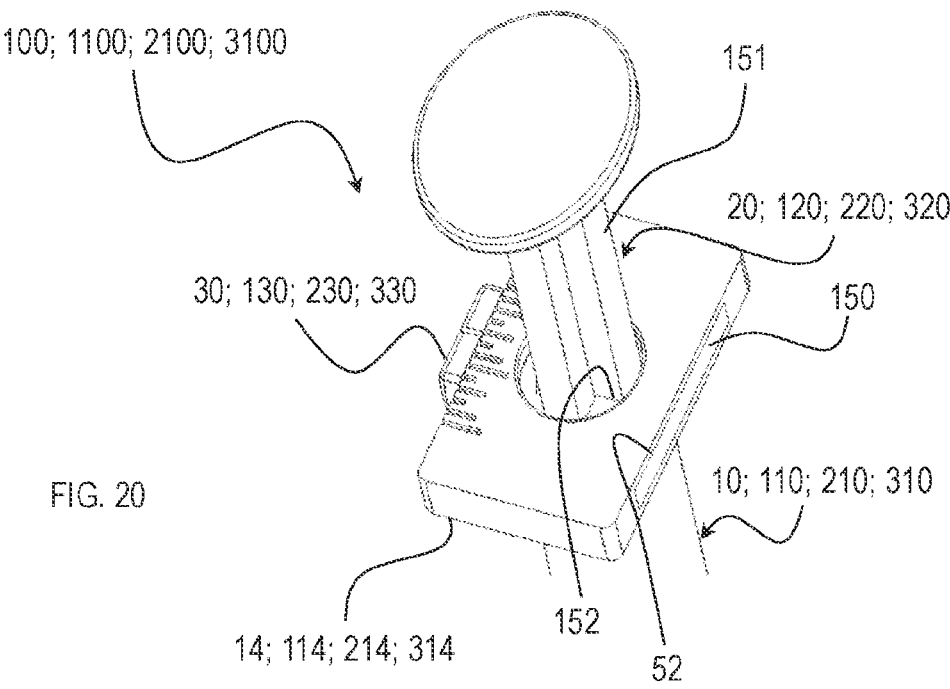
FIG. 20 is a partial perspective view, similar to that of FIG. 20, that shows a variant of the anti-rotation element of the plunger with respect to the hollow cylindrical body.

With reference to FIGS. 19 and 20, they illustrate in detail an anti-rotation element of the plunger within the hollow cylindrical body, according to two embodiments of the invention.

The anti-rotation element can be included in the dosing syringes 100, 1100, 2100 and 3100 when the hollow cylindrical body and the plunger have a different cross section from an elliptical one, e.g., circular.

With reference to FIG. 19, the anti-rotation element is comprised of a plate-shaped element 50 housed in a slot 52 formed in the flange 14, 114, 214, 314 of the hollow cylindrical body 10, 110, 210, 310 on the opposite side to the one in which the slidable housing slot 15, 115, 215a, 315 of the slider 30, 130, 230, 330 is formed, so as to abut against a wall 51 formed in the plunger 20, 120, 220, 320.

In the variant shown in FIG. 20, the anti-rotation element is comprised of a plate-shaped element 150 provided with a seat 152, housed in the slot 52 formed in the flange 14, 114, 214, 314 of the hollow cylindrical body 10, 110, 210, 310.

When in position within the slot 52, the seat 152 houses a longitudinal projection 151 formed in the plunger 20, 120, 220, 320.

Figure 21:
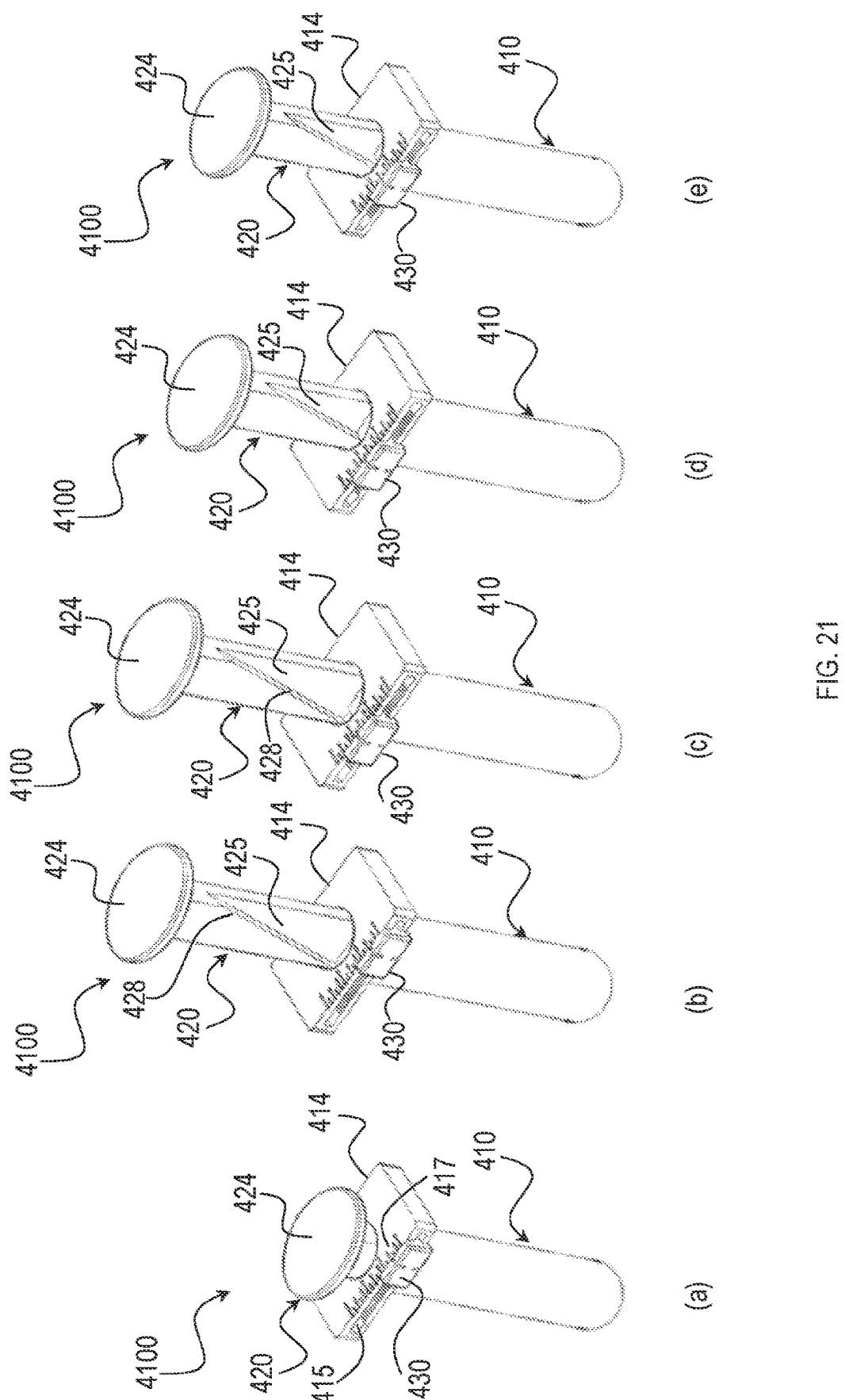
FIG. 21 (*a*) is a perspective view of a dosing syringe according to a fifth alternative embodiment of the present invention, in an operating position of the plunger and of the slider.

With reference to FIGS. 21 (a)-(e), they illustrate a dosing syringe according to a fifth alternative embodiment of the present invention.

The dosing syringe, indicated in general with reference number 4100, is very similar to the dosing syringe 100, from which it differs due to the different configuration of the longitudinal recess formed in the plunger. Thanks to the different configuration of the longitudinal recess, the dosing syringe 4100 enables the maximum quantity of product to be aspirated within the hollow cylindrical body and only the dispensed quantity, and not the aspirated quantity, of product or pharmaceutical product, to be controlled.

The dosing syringe 4100 therefore has a hollow cylindrical body 410, adapted to contain a volume of product or pharmaceutical product to be dispensed, and a plunger 420 slidable within the hollow cylindrical body 410. In the embodiment illustrated, the hollow cylindrical body 410 and the plunger 420 have an elliptical cross section. Alternatively, the hollow cylindrical body 410 and the plunger 420 can have a circular cross section, in which case an anti-rotation element of the type described above is provided.

The hollow cylindrical body 410 has a distal flange 414 provided with a longitudinal slot 415 for the slidable housing of a slider 430, having the function of blocking the stroke of the plunger 420 within the hollow cylindrical body 410, in order to control the quantity of product to be dispensed from the dosing syringe 4100. On the distal flange 414 a series of measurement notches 417 is provided, preferably accompanied by a number indicating the volume of product in millilitres.

In the plunger 420 a longitudinal recess 425 is formed, comprising an edge having an inclined portion 428 preferably extending for the entire width of the plunger 420, so that the width of the longitudinal recess increases moving from top to bottom and from right to left along the plunger 420.

The inclined portion 428 acts as an abutting and blocking wall of the slider 430 during the sliding thereof within the longitudinal slot 415 of the flange 414 of the hollow cylindrical body 410, so as to create an actual mechanical abutment that stops the stroke of the plunger 420 at the desired volume or dose of product to be dispensed.

Naturally, for the dosing syringe 4100 all the embodiments previously described can be provided. For example, it is possible to provide various longitudinal recesses, arranged on the same side or on opposite sides in the hollow cylindrical body and the edge of the longitudinal recess can be configured with steps.

The operation of the dosing syringe 4100 is as follows.

It is assumed that a user wishes to dispense a predetermined, controlled, and repeatable quantity of a product, e.g., a syrup to be administered to a child.

For that purpose, the dosing syringe 4100 is coupled to a bottle containing the syrup, typically by the interposition of an adapter and the user, by acting on the head 424, makes the plunger 420 slide within the hollow cylindrical body 410, until the complete filling of the syringe 4100 with the desired product.

At this point, the user makes the slider 430, which is in its disengaged or sliding position, slide until it is brought to the notch of the series of measurement notches 417 corresponding to the volume of product to be dispensed. Subsequently, the user pushes the slider 430 towards the inside of the slot 415, therefore orthogonally to the sliding direction, so as to block it as previously described. The quantity of product to be dispensed is thus fixed.

Should the user instead wish to set a different volume of product to be dispensed, he/she must push the slider 430 outwards, so as to bring it back into the disengaged position. Subsequently, the user makes the slider 430 slide until it is brought to the notch of the series of measurement notches 417 corresponding to the new volume of product to be dispensed.

Instead of reading the quantity of product to be dispensed on the series of notches 417, it is possible to provide one or more mechanical abutments in the longitudinal recess 425. In this case the slider 430, during its sliding movement, hits against a corresponding mechanical abutment stopping its movement. At this point, the desired dose of product can be dispensed.

To repeat the operation, it is necessary to unblock the slider 430, make it slide until it is engaged against the subsequent mechanical abutment, block the slider 430 again and proceed to dispense the new dose of product.

From the above description the features of the dosing syringe of the present invention, as well as the advantages thereof, are evident.

Finally, it is clear that the dosing syringe thus conceived is susceptible to numerous modifications and variants; furthermore, all the details can be replaced with other technically equivalent elements. In practice, the materials used, as well as the dimensions thereof, can be of any type according to the technical requirements.

The invention claimed is:

1. A dosing syringe comprising:
a hollow cylindrical body;
a plunger slidable within the hollow cylindrical body; and
at least one slider slidable within a distal flange of said hollow cylindrical body transversely to the hollow cylindrical body;
wherein at least one wall is formed in the plunger for abutting and blocking the at least one slider during sliding of the at least one slider within the distal flange;
wherein said at least one wall provides a mechanical stop configured to stop a stroke of said plunger at a predetermined volume of product to be aspirated and/or dispensed;
wherein said at least one slider comprises a first portion projecting from the distal flange and a second portion projecting orthogonally from the first portion and housed within a respective slot of the distal flange;
wherein longitudinal ribs are formed in said second portion, which are configured to slide within respective longitudinal grooves formed in the respective slot of the distal flange;
wherein longitudinal and opposite grooves for blocking the at least one slider into position are formed in said respective slot of the distal flange; and
wherein said longitudinal and opposite grooves have a complementary and slightly smaller shape than that of the longitudinal ribs.

2. The dosing syringe according to claim 1, wherein the longitudinal ribs and the respective longitudinal grooves are complementary, the respective longitudinal grooves having a slightly larger shape than that of the longitudinal ribs.

3. The dosing syringe according to claim 1, wherein said second portion of the at least one slider has at least one undercut at a free end of said second portion, wherein each undercut of the at least one undercut delimits a surface adapted to abut, in use, against a respective one of said at least one wall of the at least one slider.

4. The dosing syringe according to claim 1, wherein at least one longitudinal recess is formed in the plunger, wherein each recess of the at least one recess comprises a bottom wall and an edge extending orthogonally with respect to said bottom wall, said at least one wall of the at least one slider comprising an inclined portion of said edge.

5. The dosing syringe according to claim 4, wherein said at least one longitudinal recess comprises a distal longitudinal recess and a proximal longitudinal recess having different depths.

6. The dosing syringe according to claim 4, wherein said at least one longitudinal recess comprises one or more longitudinal recesses arranged on opposite sides of the plunger and said at least one slider comprises a pair of sliders slidable on opposite sides of the distal flange.

7. The dosing syringe according to claim 4, wherein said inclined portion extends for a whole width of the plunger, such that a width of the at least one longitudinal recess decreases moving from top to bottom and from left to right along the plunger.

8. The dosing syringe according to claim 4, wherein said inclined portion extends for a whole width of the plunger, such that a width of the at least one longitudinal recess increases moving from top to bottom and from right to left along the plunger.

9. The dosing syringe according to claim 4, wherein said inclined portion has a stepped profile.

10. The dosing syringe according to claim 1, wherein said hollow cylindrical body and said plunger have an elliptical cross-section.

11. The dosing syringe according to claim 1, wherein said hollow cylindrical body and said plunger have a circular cross section, the dosing syringe further comprising an anti-rotation element of the plunger within the hollow cylindrical body, the anti-rotation element comprising a plate-shaped element configured to be removably housed in a respective slot formed in the distal flange of the hollow cylindrical body on an opposite side to that on which a sliding housing slot of the at least one slider is formed, so as to abut against a wall formed in the plunger.

12. The dosing syringe according to claim 1, wherein a series of measurement notches of the product to be dispensed is provided on the hollow cylindrical body and/or on the distal flange.

13. A dosing syringe comprising:

a hollow cylindrical body;

a plunger slidable within the hollow cylindrical body; and at least one slider slidable within a distal flange of said hollow cylindrical body transversely to the hollow cylindrical body;

wherein at least one wall is formed in the plunger for abutting and blocking the at least one slider during sliding of the at least one slider within the distal flange;

wherein said at least one wall provides a mechanical stop configured to stop a stroke of said plunger at a predetermined volume of product to be aspirated and/or dispensed;

wherein said hollow cylindrical body and said plunger have a circular cross section, the dosing syringe further comprising an anti-rotation element of the plunger within the hollow cylindrical body, the anti-rotation element comprising a plate-shaped element configured to be removably housed in a respective slot formed in the distal flange of the hollow cylindrical body on an opposite side to that on which a sliding housing slot of the at least one slider is formed, so as to abut against a wall formed in the plunger.

* * * * *